United States Patent
Janssens et al.

(10) Patent No.: US 7,253,327 B2
(45) Date of Patent: Aug. 7, 2007

(54) METHOD OF MANUFACTURE OF A HYDROFLUOROALKANE

(75) Inventors: Francine Janssens, Vilvoorde (FR); Veronique Mathieu, Wavre (FR)

(73) Assignee: Solvay S.A. (BE)

( * ) Notice: Subject to any disclaimer, the term of this patent is extended or adjusted under 35 U.S.C. 154(b) by 0 days.

(21) Appl. No.: 11/416,000

(22) Filed: May 2, 2006

(65) Prior Publication Data

US 2006/0199982 A1 Sep. 7, 2006

Related U.S. Application Data

(63) Continuation of application No. 11/039,599, filed on Jan. 19, 2005, now abandoned.

(30) Foreign Application Priority Data

Jan. 30, 2004 (FR) .................................. 04 00921

(51) Int. Cl.
*C07C 17/42* (2006.01)

(52) U.S. Cl. ..................................................... 570/102

(58) Field of Classification Search .................. 570/102
See application file for complete search history.

(56) References Cited

U.S. PATENT DOCUMENTS

| 5,306,850 | A |   | 4/1994  | Darago                     |
|-----------|---|---|---------|----------------------------|
| 5,366,662 | A | * | 11/1994 | Barthelemy et al. ......... 252/393 |
| 5,538,665 | A | * | 7/1996  | Paulus et al. ................. 252/67 |
| 5,560,869 | A | * | 10/1996 | Barthelemy et al. ......... 252/372 |
| 5,623,150 | A | * | 4/1997  | Barthelemy et al. ... 252/182.24 |
| 5,932,775 | A |   | 8/1999  | Lacroix et al.             |
| 6,179,967 | B1 |  | 1/2001  | Nishimura et al.           |

FOREIGN PATENT DOCUMENTS

EP 0 564 036 10/1993

* cited by examiner

*Primary Examiner*—J. Parsa
(74) *Attorney, Agent, or Firm*—Connolly Bove Lodge & Hutz LLP

(57) ABSTRACT

Method of manufacture of a hydrofluoroalkane comprising the use of a Lewis base as stabilizer of the hydrofluoroalkane. No drawings.

21 Claims, No Drawings

METHOD OF MANUFACTURE OF A HYDROFLUOROALKANE

RELATED APPLICATIONS

This application is a continuation of application Ser. No. 11/039,599, filed Jan. 19, 2005, which claims benefit to French Application No. 04.00921, filed Jan. 30, 2004.

The present invention relates to a method of manufacture of a hydrofluoroalkane and a stabilized hydrofluoroalkane.

Hydrofluoroalkanes can be used, for example, as a blowing agent for polyurethane foams or as a constituent of solvent compositions.

Patent application EP-A-0564036 generally envisages the stabilization of hydrofluoroalkanes with, preferably, amylene and describes stabilization during distillation of 1,1-dichloro-1-fluoroethane (HCFC-141b) against its dehydrochlorination with this compound.

During manufacture of hydrofluoroalkanes, notably by (hydro)fluorination of a chlorinated precursor, the formation of olefinic impurities is often observed, which formation is associated at least partially with dehydrofluorination of the hydrofluoroalkane, for example during purification operations such as distillation.

It was desirable to possess a means of reducing the dehydrofluorination of hydrofluoroalkanes during their manufacture.

Accordingly, the invention relates to a method of manufacture of a hydrofluoroalkane comprising the use of a Lewis base as stabilizer of the hydrofluoroalkane.

Generally, in the course of the method of manufacture of the hydrofluoroalkane, Lewis base is added to the hydrofluoroalkane, so as to form a stabilized hydrofluoroalkane. In the sense of the invention, "method of manufacture" relates in particular to stages of purification of a hydrofluoroalkane, said hydrofluoroalkane resulting for example from a stage of synthesis by hydrofluorination of a suitable precursor for example saturated or unsaturated, chlorinated or chlorofluorinated precursors.

The Lewis base often contains at least one heteroatom and is preferably selected from alcohols, amines, amides, nitriles and phosphorus-containing compounds.

An aliphatic alcohol, in particular unsubstituted, selected from methanol, ethanol, n-propanol, isopropanol, n-butanol, isobutanol, tert-butanol and the pentanols is more particularly preferred. N-propanol and/or isopropanol, in particular isopropanol is quite particularly preferred.

In a particular embodiment, the alcohol is a polyol, preferably a diol. Ethylene glycol is preferred as diol.

As amines that can be used as Lewis base, mention may be made of the aliphatic amines or the aromatic amines. Among the aliphatic amines, the primary amines, the secondary amines and the tertiary amines are to be mentioned in particular. In general, the alkanolamines, the alkylamines, such as for example ethanolamine, n-butyl amine, tert-butylamine, n-propyl amine, isopropylamine, benzylamine, hexamethylene diamine, diethylamine, triethylamine or aromatic amines such as pyridine or aniline are used as amine.

Among the nitriles that can be used as Lewis base, mention may be made of notably aliphatic nitriles, notably acetonitrile, propionitrile, or adiponitrile and aromatic nitriles, notably benzonitrile or toluinitrile. Among the nitriles, propionitrile and adiponitrile are preferred.

Among the amides that can be used as Lewis base, mention may be made of the linear amides such as N,N-dimethylacetamide and N,N-dimethylformamide and cyclic amides such as N-methylpyrrolidone mention may also be made of hexamethylphosphoramide.

Among the phosphorus-containing compounds that can be used as Lewis base, mention may be made of notably trialkylphosphine oxides and trialkyl phosphates.

Among the trialkylphosphine oxides that can be used, mention may be notably made of the compounds of formula (R1R2R3)PO, in which R1, R2 and R3 represent identical or different C3–C10 alkyl groups, preferably linear. The following are used in particular: tri(n-butyl)phosphine oxide, tri(n-hexyl)phosphine oxide, tri(n-octyl)phosphine oxide, n-octyldi(n-hexyl)-phosphine oxide and n-hexyldi(n-octyl) phosphine oxide and mixtures thereof.

Among the trialkyl phosphates, mention may notably be made of the compounds of formula $(RO)_3PO$, in which R represents a C3–C10 alkyl group, preferably linear. Tributyl phosphate is used in particular.

Preferably, the Lewis base does not form an azeotrope with the hydrofluoroalkane. This makes it possible to improve the overall economics of the method since the Lewis base can be separated easily and reused without formation of undesirable azeotropic fractions of hydrofluoroalkane containing substantial amounts of Lewis base.

In the method according to the invention, generally from 1 to 10 000 mg, preferably from 50 to 1000 mg of Lewis base is used per kg of hydrofluoroalkane.

In the method according to the invention, the hydrofluoroalkane generally contains at least one Lewis acid, in particular iron compounds, more particularly ferric chloride. In this case the content of Lewis acid in the hydrofluoroalkane is generally from 0.1 to 500 and more often from 1 to 100 mg/kg of hydrofluoroalkane.

In the method according to the invention, the stabilized hydrofluoroalkane is generally subjected to a temperature from 50 to 200° C., for example during a purification treatment.

In the method according to the invention, the Lewis base is preferably employed during purification of the hydrofluoroalkane, in particular during a distillation stage.

Accordingly, a particular embodiment of the method according to the invention comprises at least one stage of distillation of the stabilized hydrofluoroalkane. Preferably the method according to the invention comprises at least two stages of distillation of the stabilized hydrofluoroalkane, one intended to remove "light" impurities and the other intended to remove "heavy" impurities. In this particular embodiment, the Lewis base is preferably added to the hydrofluoroalkane before it is subjected to distillation. It can also be added in a distillation column.

"Hydrofluoroalkane" is intended to denote an alkane consisting of atoms of carbon, hydrogen and fluorine. The hydrofluoroalkane is often selected from 1,1-difluoroethane, 1,1,1-trifluoroethane, 1,1,1,2-tetrafluoroethane, pentafluoroethane, 1,1,1,3,3-pentafluoropropane, 1,1,1,3,3,3-hexafluoropropane, 1,1,1,2,3,3,3-heptafluoropropane, 1,1,1,3,3-pentafluorobutane and 1,1,1,2,3,4,4,5,5,5-decafluoropentane. Preferably, it is selected from 1,1,1,3,3-pentafluoropropane and 1,1,1,3,3-pentafluorobutane. 1,1,1,3,3-pentafluorobutane is more particularly preferred.

The invention also relates to a stabilized hydrofluoroalkane containing from 1 to 500 mg/kg of a Lewis base. It was found that the stated content of Lewis base in the hydrofluoroalkane makes it possible to minimize its potential dehydrofluorination, for example during its use or its storage.

The examples given below are intended to illustrate the invention though without limiting it.

EXAMPLE 1

Stabilization of 1,1,1,3,3-pentafluorobutane by isopropanol 25 mg of $FeCl_3$ and 125 mg of isopropanol were placed with 25 g of 1,1,1,3,3-pentafluorobutane in a sealed penicillin bottle. The 1,1,1,3,3-pentafluorobutane contained 153 mg olefins/kg initially. The medium was placed in a stove regulated at 50° C. for 7 h. A sample of the liquid phase was then taken for analysis by gas chromatography. An olefins content of 152 mg/kg was measured, which corresponds to the amount present in the initial sample. The same reaction medium was heated at 70° C. for a further 7 days. The olefins content measured in the liquid phase was 141 mg/kg.

EXAMPLE 2

Stabilization of 1,1,1,3,3-pentafluorobutane by ethylene glycol 25 mg of $FeCl_3$ and 125 mg of ethylene glycol were placed with 25 g of 1,1,1,3,3-pentafluorobutane in a sealed penicillin bottle. The 1,1,1,3,3-pentafluorobutane contained 153 mg olefins/kg initially. The medium was placed in a stove regulated at 70° C. for 7 h. A sample of the liquid phase was then taken for analysis by gas chromatography. An olefins content of 152 mg/kg was measured, which corresponds to the amount present in the initial sample.

EXAMPLE 3 (COMPARATIVE)

Test of Stability in the Presence of $FeCl_3$ Only 25 mg of $FeCl_3$ was placed with 25 g of 1,1,1,3,3-pentafluorobutane in a sealed penicillin bottle. The 1,1,1,3,3-pentafluorobutane contained 153 mg olefins/kg initially. The medium was placed in a stove regulated at 50° C. for 7 h. A sample of the liquid phase was then taken for analysis by gas chromatography. An olefins content of 250 mg/kg was measured, i.e. an increase in the concentration of olefins of 98 mg/kg relative to the amount present in the initial sample. The same reaction medium was heated at 70° C. for a further 7 days. The olefins content measured in the liquid phase was 368 mg/kg.

EXAMPLE 4

Distillation of 1,1,1,3,3-pentafluorobutane with and without isopropanol

Purification of 1,1,1,3,3-pentafluorobutane was carried out by means of two distillation stages:

The 1,1,1,3,3-pentafluorobutane (without isopropanol) feeding the first distillation contained between 10 and 20 mg/kg of olefins. In the presence of ferric chlorides (at concentrations between 20 and 300 mg/kg) at the base of the second distillation, degradation of the 1,1,1,3,3-pentafluorobutane was observed. The latter was characterized by re-formation of olefins, the concentrations of which were from 40 to 60 mg/kg at discharge from the second distillation.

300 to 500 mg/kg of isopropanol was added to the 1,1,1,3,3-pentafluorobutane feeding the first distillation column. No further degradation of the 1,1,1,3,3-pentafluorobutane was observed in the second distillation and the contents of olefin at discharge from this stage were between 10 and 20 mg/kg.

The invention claimed is:

1. Method of reducing the dehydrofluorination of hydrofluoroalkane during the manufacture of the hydrofluoralkane which comprises adding a Lewis base as stabilizer to the hydrofluoroalkane in which from 1 to 10 000 mg of Lewis base is used per kg of hydrofluoroalkane in which the Lewis base is employed during purification of the hydrofluoroalkane and wherein said Lewis Base comprises an alcohol, amide, nitrile or phosphorus-containing compound and the hydrofluoroalkane contains at least one Lewis Acid.

2. Method according to claim 1, in which the Lewis base contains at least one heteroatom.

3. Method according to claim 1, in which the Lewis base is ethylene glycol or an aliphatic alcohol wherein said aliphatic alcohol is methanol, pentanol, ethanol, n-propanol, isopropanol, n-butanol, isobutanol, or tert-butanol.

4. Method according to claim 3, in which the Lewis base is isopropanol.

5. Method according to claim 1, in which the Lewis base does not form an azeotrope with the hydrofluoroalkane.

6. Method according to claim 1, in which from 1 to 10 000 mg of Lewis base is used per kg of hydrofluoroalkane.

7. Method according to claim 1, in which the content of Lewis acid in the hydrofluoroalkane is from 0.1 to 500 mg/kg of hydrofluoroalkane.

8. Method according to claim 1, in which the stabilized hydrofluoroalkane is subjected to a temperature from 50 to 200° C.

9. Method according to claim 1, comprising a stage of distillation of a stabilized hydrofluoroalkane.

10. Method according to claim 1, in which the hydrofluoroalkane is selected from the group consisting of 1,1-difluoroethane, 1,1,1-trifluoroethane, 1,1,1,2-tetrafluoroethane, pentafluoroethane, 1,1,1,3,3-pentafluoropropane, 1,1,1,3,3,3-hexafluoropropane, 1,1,1,2,3,3,3-heptafluoropropane, 1,1,1,3,3-pentafluorobutane and 1,1,1,2,3,4,4,5,5,5-decafluoropentane.

11. Method according to claim 10, in which the hydrofluoroalkane is selected from the group consisting of 1,1,1,3,3-pentafluoropropane and 1,1,1,3,3-pentafluorobutane.

12. Stabilized hydrofluoroalkane containing from 1 to 500 mg/kg of a Lewis base and a Lewis acid wherein said Lewis Base comprises amide, nitrile, phosphorus-containing compound or an alcohol.

13. Stabilized hydrofluoroalkane according to claim 12, selected from 1,1,1,3,3-pentafluoropropane and 1,1,1,3,3-pentafluorobutane.

14. Stabilized hydrofluoroalkane according to claim 12, in which the content of Lewis acid in the hydrofluoroalkane is from 0.1 to 500 mg/kg of hydrofluoroalkane.

15. Method according to claim 1, in which the Lewis base is an alcohol, amine or phosphorus-containing compound.

16. Method according to claim 1, in which the Lewis acid is an iron compound.

17. Stabilized hydrofluoroalkane according to claim 12, in which the Lewis acid is an iron compound.

18. Stabilized hydrofluoroalkane containing from 1 to 10,000 mg/kg of isopropanol and a Lewis acid.

19. The hydrofluoralkane as claimed in claim 12, wherein said Lewis Base comprises amide, nitrile, phosphorus-containing compound, n-butanol, isobutanol, tert-butanol or pentanol.

20. The hydrofluoralkane as claimed in 19, containing from 1 to 500 mg/kg of the Lewis base.

21. Stabilized hydrofluoroalkane containing from 1 to 10,000 mg/kg of a stabilizer wherein the stabilizer consists of an amide, a nitrile or a phosphorus-containing compound.

* * * * *

UNITED STATES PATENT AND TRADEMARK OFFICE
CERTIFICATE OF CORRECTION

PATENT NO. : 7,253,327 B2
APPLICATION NO. : 11/416000
DATED : August 7, 2007
INVENTOR(S) : Francine Janssens et al.

It is certified that error appears in the above-identified patent and that said Letters Patent is hereby corrected as shown below:

On the Title Page (75):

In the Inventor: "Francine Janssens, Vilvoorde (FR); Veronique, Mathieu, Wavre (FR)"

should read -- Francine Janssens, Vilvoorde (BE); Veronique Mathieu, Wavre (BE) --.

In the Claims:

In Claim 12, in column 4 line 40, "Stabilized hydrofluoroalkane containing from 1 to 500 mg/kg" should read -- Stabilized hydrofluoroalkane containing from 1 to 10,000 mg/kg --.

Signed and Sealed this

Twenty-ninth Day of January, 2008

JON W. DUDAS
*Director of the United States Patent and Trademark Office*